United States Patent [19]

Sauter et al.

[11] 4,297,364
[45] Oct. 27, 1981

[54] α-AZOLYL-α-PHENYLACETIC ACID DERIVATIVES

[75] Inventors: Hubert Sauter; Bernd Zeeh, both of Ludwigshafen; Costin Rentzea, Heidelberg; Ernst-Heinrich Pommer, Limburgerhof, all of Fed. Rep. of Germany

[73] Assignee: BASF Aktiengesellschaft, Fed. Rep. of Germany

[21] Appl. No.: 83,243

[22] Filed: Oct. 10, 1979

[30] Foreign Application Priority Data

Oct. 18, 1978 [DE] Fed. Rep. of Germany ....... 2845293

[51] Int. Cl.³ .................... A01N 43/64; A01N 43/84; C07D 249/08; C07D 401/06
[52] U.S. Cl. .................................. 424/267; 424/245; 424/248.56; 424/269; 544/64; 544/132; 546/2; 546/210; 548/101; 548/262
[58] Field of Search ...................... 548/101, 262, 341; 544/64, 132; 546/2, 210; 424/245, 269, 248.56, 269

[56] References Cited

U.S. PATENT DOCUMENTS

| 3,732,242 | 5/1973 | Buchel et al. ................. 548/341 |
| 4,073,923 | 2/1978 | Balasubramanyan et al. ..... 548/341 |
| 4,073,925 | 2/1978 | Balasubramanyan et al. ..... 548/341 |
| 4,079,143 | 3/1978 | Balasubramanyan et al. ..... 548/262 |

FOREIGN PATENT DOCUMENTS 1535777 12/1978 United Kingdom ............. 548/262

Primary Examiner—Alton D. Rollins
Attorney, Agent, or Firm—Keil & Witherspoon

[57] ABSTRACT

New compounds of the formula

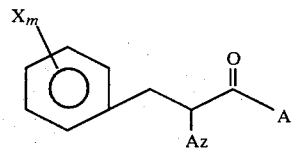

which have a good fungicidal action, their manufacture, fungicides containing these compounds as active ingredients, and processes for combating fungi with these compounds.

4 Claims, No Drawings

α-AZOLYL-α-PHENYLACETIC ACID DERIVATIVES

The present invention relates to new and valuable α-azolyl-α-phenylacetic acid derivatives, their salts and metal complexes, processes for their manufacture, and their use as fungicides.

It has been disclosed that triazole derivatives, e.g., t-butyl α-phenyl-α-1,2,4-triazol-1-yl-acetate (German Laid-Open Application DE-OS 2,638,470), have a good fungicidal action. However, this action is not always satisfactory at low application rates and use concentrations. Furthermore, the fungitoxic action is often accompanied by high phytotoxicity; consequently, when they are used in the concentrations necessary for combating fungi in crops, the crop plants are damaged. For these reasons, they are not always suitable as fungicides in the crop protection field and not suited for use in all plant species.

We have now found compounds which exhibit a good action on injurious fungi, especially from the Ascomycetes and Basidiomycetes classes, and Phycomycetes.

The object of the invention is to provide novel α-azolyl-α-phenylacetic acid derivatives of the formula

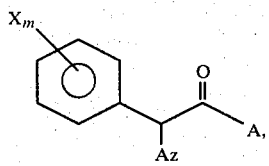

where X denotes hydrogen, fluorine, chlorine or bromine, m denotes one of the integers 1, 2 and 3, A denotes OR, R denoting alkyl, cycloalkyl, alkenyl or alkynyl, each of a maximum of 12 carbon atoms, or aryl or aralkyl of a maximum of 12 carbon atoms which may or may not be substituted by 1, 2 or 3 alkyl or alkoxy groups of 1 to 4 carbon atoms, halogen, trifluoromethyl, cyano and/or by nitro, or A denoting $NR^1R^2$, $R^1$ and $R^2$ being identical or different and each denoting hydrogen, alkyl, cycloalkyl, alkenyl or alkynyl, each of a maximum of 12 carbon atoms, or aryl or aralkyl of a maximum of 12 carbon atoms which may or may not be substituted by 1, 2 or 3 alkyl or alkoxy groups of 1 to 4 carbon atoms, halogen, trifluoromethyl, cyano and/or by nitro, or $R^1$ and $R^2$ together with N forming a saturated ring with 4 to 8 ring members which may additionally contain an oxygen or sulfur atom and may or may not be substituted by 1 to 4 halogen atoms or alkyl groups of 1 to 4 carbon atoms, and Az denotes imidazol-1-yl or 1,2,4-triazol-1-yl, A being, when X is hydrogen, $NR^1R^2$, $R^1$ and $R^2$ not being hydrogen, and their acid addition salts and metal complexes.

Examples of meanings for R are methyl, n-propyl, isopropyl, t-butyl, t-amyl, n-octyl, cyclohexyl, allyl, propargyl, benzyl, and 4-chlorobenzyl.

Examples of meanings for $R^1$ and $R^2$ are hydrogen, methyl, ethyl, n-propyl, isopropyl, n-butyl, isobutyl, t-butyl, isopentyl, t-amyl, n-hexyl, 2-ethylhexyl, cyclohexyl, allyl, propargyl, 1-butyn-3-yl, phenyl, 4-chlorophenyl, 2,4-dichlorophenyl, 4-fluorophenyl, 2-fluorophenyl, 4-bromophenyl, 3-trifluoromethylphenyl, benzyl, 4-chlorobenzyl, 2,4-dichlorobenzyl, and 4-fluorobenzyl.

$R^1$ and $R^2$ may also, together with N, form a saturated ring; A then denotes for instance pyrrolidino, piperidino, 2,6-dimethylpiperidino, morpholino, or 2,6-dimethylmorpholino.

Of the active ingredients of the formula I, two groups are preferred. The first group embraces compounds in which $X_m$ is 2—Cl, 4—Cl or 2,4—$Cl_2$ and A and Az have the above meanings. The second group comprises the compounds in which A is $NR^1R^2$, $R^1$ and $R^2$ not denoting hydrogen, and X, m and Az have the above meanings.

Examples of acid addition salts are hydrochlorides, bromides, sulfates, nitrates, phosphates, oxalates and dodecylbenzene sulfonates. As the action of the salts is attributable to the action, any anion may be selected.

Metal complexes are compounds of the formula

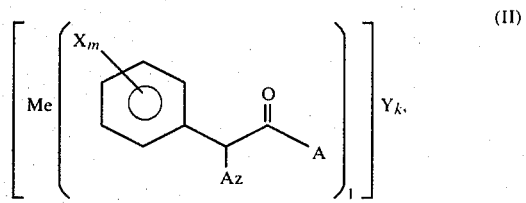

where X, m, A and Az have the above meanings, Me denotes a metal, e.g., copper, zinc, tin, manganese, iron, cobalt and nickel, Y denotes the anion of an inorganic acid, e.g., hydrochloric acid, sulfuric acid, phosphoric acid and hydrobromic acid, and l and k denote one of the integers 1, 2, 3 and 4.

A further object of the invention is to provide a process for the manufacture of compounds of the formula I, wherein an α-halocarboxylic acid derivative of the formula

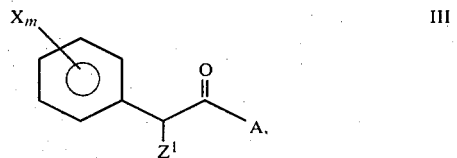

where X, m and A have the above meanings and $Z^1$ denotes a chlorine or bromine atom, is reacted with an azole HAz, where Az has the above meanings, in the presence or absence of a base and/or a solvent or diluent.

For the preparation of the new compounds, it is advisable to react the α-halocarboxylic acid derivatives of the formula III, in the presence or absence of a solvent or diluent, with about 0.5 to 2 equivalents of an alkali metal salt of the azole concerned —if desired, with the addition of a base—, at from about 0° to 200° C., preferably 20° to 160° C., and in homogeneous or nonhomogeneous phase. Examples of solvents or diluents which may be used are methanol, ethanol, isopropanol, n-butanol, diethyl ether, tetrahydrofuran, dioxane, dimethyl sulfoxide, chloroform, methylene chloride, toluene and, preferably, acetone, acetonitrile and dimethylformamide. Examples of bases which may be used are organic amines, such as triethylamine and pyridine, and inorganic compounds, such as potassium carbonate and sodium hydroxide.

The compounds of the formula III used as starting materials may be manufactured by acylation of an alcohol of the formula HOR or of an amine of the formula HNR$^1$R$^2$, where R, R$^1$ and R$^2$ have the above meanings, with an α-halocarboxylic acid halide of the formula

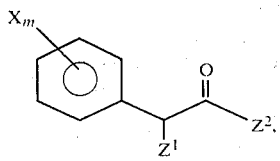    IV where X, m and Z$^1$ have the above meanings and Z$^2$ is a chlorine or bromine atom, by conventional methods (cf, e.g., "Organikum", 7.1.5.1 and 7.1.5.2, VEB Deutscher Verlag der Wissenschaften, 14th ed., Berlin, 1975).

The α-halocarboxylic acid halides of the formula IV are accessible by reaction of the corresponding mandelic acids by conventional halogenation processes, e.g., by reaction with thionyl chloride, thionyl bromide, phosphoryl chloride, or phosphorus pentachloride.

The compounds of the formula IV may also be obtained by conventional methods from phenylacetic acids by reaction to give the corresponding acid halides, e.g., with thionyl chloride, thionyl bromide or phosphorus tribromide, followed by the introduction of Z$^1$ by reaction with bromine, chlorine, sulfuryl chloride or N-bromosuccinimide (cf. E. Schwenk, D. Papa, J. Amer. Chem. Soc., 70, 3626, 1948, and P. Truitt, D. Mark, L. M. Long, J. Jeanes, ibid., 70, 4214, 1948).

The active ingredients of the formula I according to the invention may be converted in conventional manner with acids to their salts, e.g., hydrochlorides, sulfates, nitrates, oxalates, formates, acetates, or dodecylbenzene sulfonates.

The active ingredients of the formula I may also be converted into metal complexes of the formula II by reaction with prior art metal salts of the formula $$MeY_k \cdot aH_2O \qquad V.$$

where Me, Y and k have the above meanings and a denotes one of the integers 0, 1, 2, 3 and 4, in the presence of a solvent. Here, Me preferably denotes metals of subgroups I, II and IV to VII of the periodic system and metals of main groups II and IV, especially copper, zinc, tin, manganese, iron, cobalt and nickel.

Suitable solvents for the manufacture of metal complexes of the formula II are all those miscible with water. Preferred examples are methanol, ethanol, isopropanol, acetone, tetrahydrofuran and dioxane. The reaction is generally carried out at from 0° C. to 100° C., preferably from 10° to 35° C.

In the active ingredients of the formula I according to the invention, the azolyl-substituted carbon atom is chiral; consequently the active ingredients are obtained as enantiomorphous mixtures which may be separated into the individual enantiomorphs. If A in formula I also contains one or several chiral centers, diastereoisomers additionally occur in the mixture which may be separated into the individual diastereoisomeric components in conventional manner, e.g., by chromatography or crystallization. However, when the active ingredients are use as fungicides, it it normally not necessary to separate the enantiomorphs or diastereoisomers.

The following examples illustrate the manufacture of the new compounds.

Preparation of the starting materials (a) A mixture of 88.4 g of 2,4-dichloromandelic acid, 120 ml of toluene, 1 ml of dimethylformamide and 143 g of thionyl chloride is heated at 50° C., with stirring, until no more gas evolves. The toluene and the excess thionyl chloride are evaporated off in vacuo, and the residue is distilled twice through a short Vigreux column. The fraction distilling over at 85°–95° C./0.13 mbar gives 45 g of α-chloro-α-2,4-dichlorophenylacetyl chloride.

$^1$H NMR (60 MHz, CDCl$_3$): δ=6.0 (1H, s), 7.1–7.6 ppm (3H, s). IR (film): 1795, 1584, 1472, 1100, 1043, 982, 864, 776, 736, 693 cm$^{-1}$.

The compound α-chloro-α-(4-chlorophenyl)-acetyl chloride, b.p.: 105°–115° C./0.53 mbar, is obtained analogously.

$^1$H NMR (60 MHz, CDCl$_3$): δ=5.6 (1H, s), 7.4 ppm (4H, m). IR (film): 1787, 1588, 1488, 1202, 1090, 1013, 980, 740, 690 cm$^{-1}$.

(b) While stirring and with ice cooling, a solution of 17.6 g of t-butanol and 19.2 ml of pyridine in 60 ml of dichloromethane is dripped into a solution, cooled at 5° C., of 62 g of α-chloro-α-(2,4-dichlorophenyl)-acetyl chloride in 60 ml of dichloromethane in such a manner that the temperature of the reaction mixture stays below 10° C. After all the solution has been dripped in, the mixture is stirred overnight at room temperature, is then diluted with 100 ml of dichloromethane and extracted 5 times, each time with 100 ml of water. The organic phase is dried over magnesium sulfate and distilled after the solvent has been evaporated. There is obtained 58 g of α-chloro-α-(2,4-dichlorophenyl)-acetic acid t-butyl ester as a colorless oil; b.p. 98°–103° C./0.13 mbar.

$^1$H NMR (60 MHz, CDCl$_3$): δ=1.4 (9H, s), 5.7 (1H, s), 7.2–7.8 (3H, m).

The following esters are prepared in the same way:
α-chloro-α-(4-chlorophenyl)-acetic acid t-butyl ester, b.p. 100° C./0.27 mbar
α-chloro-α-(2,4-dichlorophenyl)-acetic acid t-amyl ester.

(c) While stirring, 15.2 g of N-2-butyl-N-methylamine is dripped into a solution of 22.4 g of α-chloro-α-(2,4-dichlorophenyl)-acetyl chloride (see a)) in 100 ml of dioxane. After the exothermic reaction has subsided, the mixture is stirred overnight and then poured into 700 ml of ice water; the resultant mixture is acidified with dilute hydrochloric acid and the oil which has precipitated is extracted 8 times, each time with 100 ml of dichloromethane. The extracts are combined, dried over magnesium sulfate and concentrated; there is obtained 17.2 g of α-chloro-α-(2,4-dichlorophenyl)-acetic acid-N-2-butyl-N-methyl amide as a colorless oil.

$^1$H NMR (60 MHz, CDCl$_3$): δ=0.5–1.8 (8H, m), 2.7–3.0 (3H, 4 singlets), 3.2–4.9 (1H, m), 7.2–7.9 (3H, m):
4 diastereoisomeric and rotational isomer components.

(d) While stirring, 22.3 g of diisopropylamine is dripped into a solution of 24.5 g of α-chloro-α-(4-chlorophenyl)-acetyl chloride (see a)) in 50 ml of dioxane. After the exothermic reaction has subsided, the mixture is stirred overnight and then poured into 700 ml of ice water; the resultant mixture is acidified with dilute hydrochloric acid and the oil which separates out is extracted 8 times, each time with 100 ml of dichloromethane. The combined extracts are washed twice with sodium carbonate solution, dried over magnesium sulfate and concentrated. There is obtained 27.2 g of α- chloro-α-(4-chlorophenyl)-acetic acid diisopropyl amide as a brownish oil.

¹H NMR (270 MHz, CDCl₃): δ=0.95 (3H, d), 1.15 (3H, d), 1.40 (3H, d), 1.45 (3H, d), 3.45 (1H, m), 4.00 (1H, m), 5.65 (1H, s), 7.40 ppm (4H, AA'BB').

IR (film): 2965, 1648, 1489, 1448, 1369, 1320, 1088, 1039, 1013, 761 cm⁻¹.

The amides of the formula III listed in Table 1, Z¹ denoting a chlorine atom, are prepared as in c and d. The compounds are generally characterized by their derivatives of the formula I (the numbers of the compounds refer in all the tables to the examples).

TABLE 1

| $X_m$ | —A | Characterized by compound no. |
|---|---|---|
| 2,4-Cl₂ | ⟶N(H)CH(CH₃)- (chiral) | 3 |
| 2,4-Cl₂ | ⟶N(H)CH(C₂H₅) | 4 |
| 2,4-Cl₂ | ⟶N(iPr)H | 5 |
| 2,4-Cl₂ | ⟶N(CH₃)₂ | 6 |
| 2,4-Cl₂ | ⟶N(iPr)₂ | 7 |
| 2,4-Cl₂ | ⟶N(iPr)(cyclohexyl) | 8 |
| 2,4-Cl₂ | ⟶N(CH₂—tetrahydrofuran) | 9 |
| 2,4-Cl₂ | ⟶N(H)CH(CH₃)CH₂— | 10 |
| 2,4-Cl₂ | ⟶N(cyclohexenyl) | 17 |
| 2,4-Cl₂ | ⟶N(iPr)CH₂Ph | 18 |
| 2,4-Cl₂ | ⟶N(iPr)(4-Cl-C₆H₄) | 20 |
| 2,4-Cl₂ | ⟶N(iPr)Ph | 21 |

PREPARATION OF THE END PRODUCTS

Example 1

α-(2,4-dichlorophenyl)-α-(1,2,4-triazolyl-1-yl)-acetic acid-N -2-butyl-N-methyl amide While stirring, 5.4 g of 1,2,4-triazole in 30 ml of dimethylformamide is dripped into a suspension of 1.6 g of sodium hydride in 50 ml of dimethylformamide, and the mixture is stirred for about 1 hour until no more gas evolves. 17.2 g of α-chloro-α-(2,4-dichlorophenyl)-acetic acid-N-2-butyl-N-methyl amide is then dripped in and, after the exothermic reaction has subsided, the mixture is stirred for a further 15 hours. The mixture is then taken up in 300 ml of dichloromethane and extracted 4 times, each time with 100 ml of water. After the organic phase has been dried and the solvent evaporated in vacuo, a pale oil remains; when it is triturated with diisopropyl ether, 9.8 g of colorless crystals of m.p. 116°–119° C. separate out.

¹H NMR (220 MHz, CDCl₃): δ=0.4–1.7 (8H, several multiples), 2.7–2.9 (3H, m), 3.2–3.8 and 4.5–4.8 (1H, 2 multiplets), 6.8–6.9 (1H, m), 7.2–7.6 (3H, m), 7.9–8.1 ppm (2H, m): 4 rotational isomer and diastereoisomeric components.

Example 2

α-(4-chlorophenyl)-α-imidazol-1-yl-acetic acid-diisopropyl amide

While stirring, a solution of 4.5 g of imidazole in 30 ml of dimethylformamide is dripped into a suspension of 1.3 g of sodium hydride in 30 ml of dimethylformamide. When no more gas evolves, a solution of 13.6 g of α-chloro-α-(4-chlorophenyl)-acetic acid-diisopropyl amide (see d)) in 100 ml of dimethylformamide is dripped in and the mixture is stirred overnight at room temperature. The oil which remains after the solvent has been evaporated off is taken up in 100 ml of dichloromethane and shaken 5 times, each time with 100 ml of 5% strength sodium chloride solution. The organic phase is then concentrated and chromatographed on silica gel (25×6 cm) using dichloromethane/acetone (9:1). After 2 l of first runnings have been separated off, the product fractions are obtained from which, after concentration and trituration with 10 ml of diisopropyl ether, 8.9 g of colorless crystals (m.p.: 112° C.) are isolated.

¹H NMR (270 MHz, CDCl₃): 0.9 (d, 3H), 1.2 (d, 3H), 1.5 (2d, 6H), 3.5 (m, 1H), 3.9 (m, 1H), 6.1 (s, 1H), 6.9 (s, 1H), 7.0 (s, 1H), 7.2–7.4 (AA'BB', 4H), 7.5 ppm (s, 1H).

The following compounds may be prepared analogously:

| No. | $X_m$ | Az | —A | m.p. (°C.) |
|---|---|---|---|---|
| 3 | 2,4-Cl₂ | 1,2,4-triazol-1-yl | ⟶N(H)CH(CH₃)- (chiral) | 167–171 |
| 4 | 2,4-Cl₂ | " | ⟶N(H)CH(C₂H₅) | 129–132 |
| 5 | 2,4-Cl₂ | " | ⟶N(iPr)H | 104–107 |

-continued

| No. | $X_m$ | Az | —A | m.p. (°C.) |
|---|---|---|---|---|
| 6 | 2,4-Cl$_2$ | " | N(CH$_3$)$_2$ | 115–119 |
| 7 | 2,4-Cl$_2$ | " | N(iPr)$_2$ | 117–120 |
| 8 | 2,4-Cl$_2$ | " | N(CH$_3$)(cyclohexyl) | 157–161 |
| 9 | 2,4-Cl$_2$ | " | N(CH$_2$-cyclopropyl)(CH$_2$CH(cyclopropyl)O-) | 131–134 |
| 10 | 2,4-Cl$_2$ | " | NH-CH(CH$_3$)-CH$_2$CH$_3$ | 156–157 |
| 11 | 2,4-Cl$_2$ | imidazol-1-yl | NH-CH(CH$_3$)-CH$_2$CH$_3$ | 123–126 |
| 12 | 4-Cl | 1,2,4-triazol-1-yl | —O-CH(CH$_3$)$_2$ | 92 |
| 13 | 2,4-Cl$_2$ | " | —O-CH(CH$_3$)$_2$ | 83–85 |
| 14 | 2,4-Cl$_2$ | " | N(CH$_3$)(sec-butyl) | 116–119 |
| 15 | 2,4-Cl$_2$ | " | —O-C(CH$_3$)(Et) | IR(film): 2965, 1743, 1465, 1260, 1130, 1002, 865, 812, 672 cm$^{-1}$ |
| 16 | " | " | N(CH$_3$)(CH(cyclohexyl)(CH$_3$)) | 121–123 |
| 17 | 2,4-Cl$_2$ | " | N(CH$_3$)(CH$_2$-CH=CH-cyclohexyl) | 111–112 |
| 18 | 2,4-Cl$_2$ | " | N(iPr)(CH$_2$Ph) | 93–97 |
| 19 | 2,4-Cl$_2$ | " | N(iPr)(n-Bu) | 81–82 |
| 20 | " | " | N(CH$_3$)(4-Cl-C$_6$H$_4$) | IR(film): 1670, 1483, 1380, 1271, 1131, 1096, 1087, 1008, 799 cm$^{-1}$ |
| 21 | " | " | N(iPr)(Ph) | 130–131 |
| 22 | 2,4-Cl$_2$ | " | N(2,6-dimethylpiperidinyl) | 148–151 |
| 23 | " | " | N(CH$_3$)(CH(CH$_3$)-) | 99–101 |
| 24 | 4-Cl | " | N(iPr)$_2$ | 123 |
| 25 | " | imidazol-1-yl | " | 112 |
| 26 | " | 1,2,4-triazol-1-yl | N(CH$_3$)(CH(CH$_3$)-) | 115 |
| 27 | 4-Cl | imidazol-1-yl | N(CH$_3$)(CH(CH$_3$)-) | IR(film): 2950, 1650, 1484, 1361, 1220, 1068, 1010, 795, 658 cm$^{-1}$ |
| 28 | 4-Cl | 1,2,4-triazol-1-yl | N(CH$_3$)(CH(CH$_3$)-n-Bu) | IR(film): 2917, 1640, 1431, 1272, 1138, 675 cm$^{-1}$ |
| 29 | " | " | N(n-pentyl)$_2$ | 2945, 2920, 1650, 1489, 1458, 1271, 1131, 1012, 793, 675 cm$^{-1}$ |
| 30 | H | " | N(iPr)$_2$ | 106 |
| 31 | " | " | N(CH$_3$)(C(CH$_3$)$_2$-) | 115 |
| 32 | H | " | N(iPr)(Ph) | IR(film): 2961, 1659, 1490, 1393, 1272, 1112, 724, 702, 675 cm$^{-1}$ |
| 33 | " | " | N(iPr)(n-Bu) | IR(film): 2950, 1650, 1494, 1450, 1419, 1272, 1197, 1127, 752, 676 cm$^{-1}$ |
| 34 | 4-Cl | " | N(CH$_3$)(CH(CH$_3$)-C≡CH) | IR(film): 3290, 2920, 1655, 1490, 1274, 1088, 1014, 672 cm$^{-1}$ |
| 35 | " | " | N(CH$_3$)(C(CH$_3$)$_2$-n-Pr) | 102–105 |
| 36 | 4-Cl | " | N(CH$_3$)(CH$_2$-CH(CH$_3$)$_2$) | 60–62 |

-continued

| No. | $X_m$ | Az | —A | m.p. (°C.) |
|---|---|---|---|---|
| 37 | " | imidazol-1-yl |  | 89–91 |
| 38 | 2-Cl | 1,2,4-triazol-1-yl |  | |
| 39 | " | " |  | |
| 40 | " | " |  | 130–132 |
| 41 | " | " |  | |
| 42 | " | " |  | |

The new compounds, and their salts and metal complexes, exhibit a broad fungicidal action and are excellently tolerated by crop plants.

Of the new compounds of the formula I, two groups are particularly preferred. The first preferred group embraces those compounds of the formula I in which $X_m$ is 2,4-dichloro and A and Az have the stated meanings. The second preferred group embraces those compounds of the formula I in which A is $NR^1R^2$ and $R^1$ and $R^2$ do not denote hydrogen; X, m and Az have the stated meanings.

The new active ingredients may also be employed in the form of their salts or metal complexes.

The compounds according to the invention are particularly suitable for combating fungus diseases in various crops, e.g., *Ustilago scitaminea, Hemileia vastatrix, Uromyces fabae* and *appendiculatus, Rhizoctonia solani, Erysiphe graminis, Uncinula necator, Sphaerotheca fuliginea, Erysiphe cichoracearum, Podosphaera leucotricha, Venturia inaequalis, Plasmopara viticola,* and *Pseudoperonospora humuli.*

By "crops", we mean in this connection especially wheat, rye, barley, oats, rice, Indian corn, apples, cucumbers, beans, coffee, sugarcane, grapes, strawberries and ornamentals in horticulture.

The active ingredients according to the invention are systemic. The systemic action of these agents is of particular interest in connection with the control of internal plant diseases, e.g., mildew in cereals.

The agents according to the invention may simultaneously suppress the growth of two or more of the abovementioned fungi. Application rates necessary for combating phytopathogenic fungi are from 0.05 to 2 kg of active ingredient per hectare of crop area.

The compounds of the invention can be converted into the conventional formulations, e.g. solutions, emulsions, suspensions, dusts, powders, pastes and granules. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95% by weight of active ingredient, preferably from 0.5 to 90%.

The formulations, and the ready-to-use preparations obtained therefrom, e.g. solutions, emulsions, suspensions, powders, dusts, pastes or granules, are applied in the conventional manner, e.g. by spraying, atomizing, dusting, treating seed, or watering.

Examples of such formulations are given below.

I. 90 parts by weight of compound 1 is mixed with 10 parts by weight of N-methyl-α-pyrrolidone. A mixture is obtained which is suitable for application in the form of very fine drops.

II. 20 parts by weight of compound 13 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound 16 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound 22 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound 21 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 16 is intimately mixed with 97 parts by weight of particulate kaolin. A dust is obtained containing 3% by weight of the active ingredient.

VII. 30 parts by weight of compound 20 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 17 is intimately mixed with 10 parts of the sodium salt of a phenolsulfonic acid-ureaformaldehyde condensate, 2 parts of silica gel and 48 parts of water to give a stable aqueous dispersion. Dilution in 100,000 parts by weight of water gives an aqueous dispersion containing 0.04 wt% of active ingredient.

IX. 20 parts of compound 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents according to the invention may also be applied in admixture with other active ingredients, e.g., herbicides, insecticides, growth regulators and other fungicides, and also with fertilizers. When admixed with other fungicides, an increase in the spectrum of action and an improvement in performance (synergism) are in many instances achieved. Examples of fungicides which may be combined with the compounds of the invention are dithiocarbamates and derivatives thereof, e.g.,
ferric dimethyldithiocarbamate
zinc dimethyldithiocarbamate
manganese ethylenebisdithiocarbamate
zinc ethylenebisdithiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene-bisdithiocarbamate) and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitrophenol derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-trichloromethylthiotetrahydrophthalimide
N-trichloromethylthiophthalimide
2-heptadecyl-2-imidazoline acetate
2,4-dichloro-6-(o-chloroanilino)-s-triazine
O,O-diethylphthalimidophosphonothioate
5-amino-1-[bis-(dimethylamino)-phosphinyl]-3-phenyl-1,2,4-triazole
5-ethoxy-3-trichloromethyl-1,2,4-thiadiazole
2,3-dicyano-1,4-dithiaanthraquinone
2-thio-1,3-dithio-[4,5-b]-quinoxaline
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
pyridine-2-thiol-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis-[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene and various fungicides, such as dodecylguanidine acetate
3-[2-(3,5-dimethyl-2-oxycyclohexyl)-2-hydroxyethyl]-glutarimide hexachlorobenzene
N-dichlorofluoromethylthio-N',N'-dimethyl-N-phenyl-sulfuric acid diamide
D,L-methyl-N-(2,6-dimethylphenyl)-N-furyl-(2)-alaninate
D,L-N-(2,6-dimethylphenyl)-N-(2'-methoxyacetyl)-alanine methyl ester
diisopropyl 5-nitroisophthalate
2,5-dimethylfuran-3-carboxylic acid anilide
2,5-dimethylfuran-3-carboxylic acid cyclohexyl amide
2-methylbenzoic acid anilide
1-(3,4-dichloroanilino)-1-formylamino-2,2,2-trichloroethane
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzenediazosodium sulfonate
2-chloro-1-nitropropane
polychloronitrobenzenes, such as pentachloronitrobenzene, methyl isocyanate, fungicidal antibiotics such as griseofulvin and kas ugamycin, tetrafluorodichloroacetone, 1-phenylthio semicarbazide, Bordeaux mixture, nickel-containing compounds and sulfur.

The following examples demonstrate the biological action of the new compounds. The compounds used for comparison purposes were $\alpha$-phenyl-$\alpha$-1,2,4-triazol-1-yl-acetic acid-t-butyl ester (Y) and $\alpha$-phenyl-$\alpha$-1,2,4-triazol-1-yl-acetic acid-t-butyl amide (Z) which are disclosed in German Laid-Open Application DE-OS No. 2,638,470.

Example A

Leaves of wheat seedlings of the "Caribo" variety grown in pots are sprayed with aqueous emulsions containing 80% of active ingredient and 20% of emulsifier (dry basis). Two days after the sprayed-on layer has dried, the plants are dusted with spores of powdery mildew (Erysiphe graminis var. tritici). The plants are then placed in a greenhouse at from 18° to 24° C. After 10 days the extent of fungus spread is assessed.

| Active ingredient | Leaf attack after spraying with liquor containing active ingredient in amounts of | | |
|---|---|---|---|
| | 0.025% | 0.012% | 0.006% |
| 5 | 0 | 0 | 1 |
| 7 | 0 | 0 | 0 |
| 8 | 1 | 1 | 1 |
| 13 | 0 | 0 | 0 |
| 14 | 0 | 0 | 4 |
| 15 | 0 | 0 | 3 |
| 16 | 0 | 0 | 0 |
| 17 | 0 | 0 | 2 |

-continued

| Active ingredient | Leaf attack after spraying with liquor containing active ingredient in amounts of | | |
|---|---|---|---|
| | 0.025% | 0.012% | 0.006% |
| 18 | 0 | 0 | 2 |
| 19 | 0 | 0 | 0 |
| 20 | 0 | 0 | 0 |
| 21 | 0 | 0 | 0 |
| 22 | 0 | 0 | 0 |
| 23 | 0 | 0 | 0 |
| 26 | 1 | 2 | 3 |
| 30 | 0 | 0 | 0 |
| 31 | 0 | 1 | 3 |
| 32 | 0 | 2 | 2 |
| 34 | 0 | 0 | 0 |
| 35 | 0 | 0 | 0 |
| 36 | 0 | 0 | 0 |
| 37 | 0 | 0 | 1 |
| 42 | 0 | 0 | 0 |
| Y | 4 | 4 | 5 |
| Z | 2 | 3 | 4 |
| Control (untreated) | 5 | | |

0 = no fungus frowth, graduated to
5 = leaf surface completely covered with fungus

Example B

Leaves of potted vines of the Müller-Thurgau variety are sprayed with aqueous suspensions containing (dry basis) 80% (wt%) of the active ingredient and 20% of sodium lignin sulfonate. 0.05 and 0.025% (dry basis) spray liquors are used. After the sprayed-on liquor has dried, the leaves are infected with a zoospore suspension of Plasmopara viticola. The plants are first placed for 16 hours in a steam-saturated (moist) chamber at 20° C., and then in a greenhouse for 8 days at from 20° to 30° C. To accelerate and intensify the sporangiophore discharge, the plants are then again placed in the moist chamber for 16 hours. The extent of the disease is then ssessed; 0 denotes no fungus attack, graduated down to 5, which denotes total attack (control).

| Active ingredient | Leaf attack after spraying with liquor containing active ingredients in amounts of | |
|---|---|---|
| | 0.05% | 0.025% |
| 16 | 0 | 0 |
| 18 | 0 | 2 |
| 19 | 0 | 1 |
| Control (untreated) | 5 | |

We claim:

1. A compound selected from the group consisting of α-(2,4-dichlorophenyl)-α-(1,2,4-triazol-1-yl)-acetic acid-t-butyl ester, α-(2,4-dichlorophenyl)-α-(1,2,4-triazol-1-yl)-acetic acid-N,N-diisopropyl amide, α-(2,4-dichlorophenyl)-α-(1,2,4-triazol-1-yl)-acetic acid-N-cyclohexyl-N-methyl amide, α-(2,4-dichlorophenyl)-α-(1,2,4-triazol-1-yl)-acetic acid-N-t-butyl-N-cyclohexyl amide, α-(2,4-dichlorophenyl)-α-(1,2,4-triazol-1-yl)-acetic acid-N-[t]n-butyl-N-isopropyl amide, α-(2,4-dichlorophenyl)-α-(1,2,4-triazol-1-yl)-acetic acid-N-4-chlorophenyl-N-methyl amide, α-(2,4-dichlorophenyl)-α-(1,2,4-triazol-1-yl)-acetic acid-N-isopropyl-N-phenyl amide, α-(2,4-dichlorophenyl)-α-(1,2,4-triazol-1-yl)-acetic acid-N-2,6-dimethylpiperidide, α-(2,4-dichlorophenyl)-α-(1,2,4-triazol-1-yl)-acetic acid-N-t-butyl-N-methyl amide, α-phenyl-α-(1,2,4-triazol-1-yl)-acetic acid-N,N-diisopropyl amide, α-(4-chlorophenyl)-α-(1,2,4-triazol-1-yl)-acetic acid-N-methyl-N-but-1-yn-3-yl amide, α-(4-chlorophenyl)-α-(1,2,4-triazol-1-yl)-acetic acid-diisobutyl amide, α-(2,4-dichlorophenyl)-α-(1,2,4-triazol-1-yl)-acetic acid-N-methyl-N-isopropyl amide, α-(2,4-dichlorophenyl)-α-(1,2,4-triazol-1-yl)-acetic acid-N-methyl-N-isobutyl amide, α-(2,4-dichlorophenyl)-α-(1,2,4-triazol-1-yl)-acetic acid-isopentyl ester, α-(2,4-dichlorophenyl)-α-(1,2,4-triazol-1-yl)-acetic acid-N-propenyl-N-cyclohexyl amide, α-(2,4-dichlorophenyl)-α-(1,2,4-triazol-1-yl)-acetic acid-N-isopropyl-N-benzyl amide, α-phenyl-α-(1,2,4-triazol-1-yl)-acetic acid-N-methyl-N-t-butyl amide, α-(4-chlorophenyl)-α-(1,2,4-triazol-1-yl)-acetic acid-N-n-butyl-N-t-butyl amide, α-(4-chlorophenyl)-α-(imidazol-1-yl)-acetic acid-N-n-butyl-N-t-butyl amide, and α-(2-chlorophenyl)-α-(1,2,4-triazol-1-yl)-acetic acid-N-isopropyl-N-phenyl amide.

2. A process for combating fungus diseases in crop plants caused by powdery mildew wherein at least one compound as claimed in claim 1 is allowed to act on the fungi at an application rate of from 0.5 to 2 kg of active ingredient per hectare of crop area.

3. A process for the prophylactic control of powdery mildew, wherein at least one compound as claimed in claim 1 is allowed to act on areas, plants or seed threatened with fungus attack at an application rate of from 0.5 to 2 kg of active ingredient per hectare of crop area.

4. A fungicidal agent for combating powdery mildew consisting essentially of from 0.1 to 95% by weight of a compound selected from the group as claimed in claim 1 and a solid or liquid carrier.

* * * * *